United States Patent
Frezza et al.

(10) Patent No.: US 11,684,586 B1
(45) Date of Patent: Jun. 27, 2023

(54) ANHYDROUS HYDROCOLLOID MATRIX COMPRISING HOMOGENEOUSLY DISTRIBUTED ENCAPSULATED THERAPEUTIC AGENTS

(71) Applicant: Peace Out, LLC, San Francisco, CA (US)

(72) Inventors: Enrico Frezza, San Francisco, CA (US); Bobbie Marshall, San Francisco, CA (US)

(73) Assignee: Peace Out, LLC, San Francisco, CA (US)

( * ) Notice: Subject to any disclaimer, the term of this patent is extended or adjusted under 35 U.S.C. 154(b) by 0 days.

(21) Appl. No.: 17/682,808

(22) Filed: Feb. 28, 2022

(51) Int. Cl.
*A61K 9/70* (2006.01)
*A61K 31/60* (2006.01)
*A61K 9/00* (2006.01)

(52) U.S. Cl.
CPC .......... *A61K 9/7038* (2013.01); *A61K 9/0014* (2013.01); *A61K 31/60* (2013.01)

(58) Field of Classification Search
None
See application file for complete search history.

(56) References Cited

U.S. PATENT DOCUMENTS

| | | | |
|---|---|---|---|
| 4,538,603 A | 9/1985 | Pawelchak et al. | |
| 5,569,207 A | 10/1996 | Gisselberg et al. | |
| 5,585,109 A | 12/1996 | Hayward et al. | |
| 5,885,237 A | 3/1999 | Kadash et al. | |
| 6,471,986 B1 | 10/2002 | Cline et al. | |
| 6,495,148 B1 | 12/2002 | Buseman et al. | |
| 8,858,988 B2 | 10/2014 | Chamberland et al. | |
| 2002/0147265 A1 | 10/2002 | Ding et al. | |
| 2003/0175333 A1* | 9/2003 | Shefer | A61K 8/671 514/61 |
| 2005/0080465 A1 | 4/2005 | Zelickson et al. | |

(Continued)

FOREIGN PATENT DOCUMENTS

CN 103143054 6/2013
CN 204683911 10/2015

(Continued)

OTHER PUBLICATIONS

Hydrocolloid PSAs: New Formulation Strategies, "MDDI Medical Device and Diagnostic Industry News Products and Suppliers" (Jun. 1, 1999) accessible at (http://www.mddionline.com/article/hydrocolloid-psas-new-formulation-strategies).

(Continued)

*Primary Examiner* — Isis A Ghali
(74) *Attorney, Agent, or Firm* — Frost Brown Todd LLP (57) ABSTRACT

Anhydrous hydrocolloid matrices contain one or more encapsulated therapeutic agents, including an acne agent and/or skin conditioning agent. The anhydrous hydrocolloid matrices are used as acne treatment dressings alone or in a laminate with a water-impermeable or semi-water impermeable backing and a release liner. The anhydrous hydrocolloid matrices are made using a premix of viscosity modifiers and hydrocarbon emollients and the one or more therapeutic agents, which are mixed via high shear mixing to form the premix. The resulting anhydrous hydrocolloid matrices include the one or more therapeutic agents which are encapsulated and homogeneously distributed therein.

9 Claims, 5 Drawing Sheets

(56) References Cited

U.S. PATENT DOCUMENTS

| | | | |
|---|---|---|---|
| 2005/0191337 A1* | 9/2005 | Gueret | A61Q 19/00 424/448 |
| 2005/0244525 A1 | 11/2005 | Callaghan et al. | |
| 2006/0253078 A1 | 11/2006 | Wu et al. | |
| 2009/0216169 A1 | 8/2009 | Hansen et al. | |
| 2013/0296762 A1 | 11/2013 | Toth | |
| 2014/0363488 A1 | 12/2014 | Hansen et al. | |
| 2017/0304215 A1* | 10/2017 | Frezza | A61K 31/60 |

FOREIGN PATENT DOCUMENTS

| | | |
|---|---|---|
| EP | 3448529 | 3/2019 |
| WO | WO 2001/013968 | 3/2001 |
| WO | WO 2002/085387 | 10/2002 |
| WO | WO 2014/159798 | 10/2014 |
| WO | WO 2017/189112 | 11/2017 |

OTHER PUBLICATIONS

World Wide Wounds: Frequently Asked Questions: Hydrocolloid Dressings (Apr. 1998) accessible at: http://www.worldwidewounds.com/1998/April/Hydrocolloid-FAQ/hydrocolloid-questions.html).

CA Examination Search Report dated May 17, 2021 for Application No. 3,022,180, 4 pages.

CA Examiner's Report dated Mar. 8, 2022 for Application No. 3,022,180, 3 pages.

Agrawal, "Irreversible Hydrocolloid Alginate", Presentation Published Online at https://www.slideshare.net/amitshravgi/alignateirreversible-hydrocolloid (Jan. 25, 2014), 37 pages.

Davies, P., "Comparison of Foam and Hydrocolloid Dressings in the Management of Wounds; a review of the published literature", available at Web page http://www.worldwidewounds.com/2010/July/DaviesRippon/DaviesRippon.html, Apr. 2010, accessed on Apr. 29, 2022.

Decker, A., "Over-the-Counter Acne Treatments", J Clin Aesthet Dermatol, May 2012, 5(5): 32-40, XP055644876, 9 pages.

Maver et al., "Functional Wound Dressing Materials with Highly Tunable Drug Release Properties", RCS Advances 5:77873-77884 (2015), 12 pages.

Swezey, L, "Hydrocolloid Dressings", available https://woundeducators.com/hydrocolloid-dressings/, Aug. 26, 2010, accessed Jan. 10, 2018, 7 pages.

Tighe and Mann, "Advanced Wound Repair Therapies", Hydrocolloid Dressing Materials: Structure and Properties, (2011), Science Direct, Table 11.3.2, 17 pages.

Tuchayi S. et al., "Acne Vulgaris", Nat Rev Dis Primers, 1 page 15029, Sep. 17, 2015, 21 pages.

Van Vugt, et al., "Biomaterials in Treatment of Orthopedic Infections", Management of Periprosthetic Joint Infections (2017), Science Direct, p. 10, 17 pages.

Zander et al. "Treatment of Acne Vulgaris with Salicylic Acid Pads", Clinical Therapeutics, Mar. 1, 1992 14(2) 247-253; PMID 153528. (Year: 1992).

\* cited by examiner

ANHYDROUS HYDROCOLLOID MATRIX COMPRISING HOMOGENEOUSLY DISTRIBUTED ENCAPSULATED THERAPEUTIC AGENTS

Hydrocolloids are a unique family of materials, and the term "hydrocolloid" that is used to described these materials is a misnomer, as it belies their nature and properties. For example, it is widely recognized that the use of the term "hydrocolloids" is not strictly correct, since these materials are composed of a compounded mixture of natural hydrophilic polymer particles (e.g., gelatin, pectin and sodium carboxymethylcellulose) dispersed in a matrix of a hydrophobic pressure-sensitive adhesive polymer. Unlike conventional sheet hydrogels, which are fully hydrated, and unlike skin-adhesive hydrogels, which are partially hydrated, hydrocolloids contain no water and the particulates contained therein are not colloidally dispersed. However, upon exposure to an aqueous fluid, the natural hydrophilic polymers that are present in a hydrocolloid, absorb moisture. As moisture absorption progresses, the phase structure of a hydrocolloid can invert, and a continuous aqueous phase may be formed in which the hydrophobic pressure-sensitive adhesive becomes dispersed. Even at very high levels of water absorption for example, beyond those that may be desirable for use in acne treatment, it is debatable whether a colloidal structure is actually formed. In any case, as components of a hydrocolloid absorb aqueous fluid, they can eventually form a soft, mobile gel.

Pressure-sensitive adhesives have been used to deliver active ingredients to wounds or skin. For example, WO 2001013968 to Lipman (hereinafter, "Lipman"), describes incorporating cyclodextrins into pressure sensitive adhesives based upon hydrophilic polymers, which are usually cross-linked. Pursuant to Lipman, the term "hydrocolloid" is specifically used to "embrace the term 'cyclodextrin'" and Lipman notes that "within the scope of the [disclosed] invention a cyclodextrin may be or may not be the only hydrocolloid present in the adhesive." The pressure sensitive adhesive compositions that contain a so-called hydrocolloid such as cyclodextrin, are described by Lipman as being "hydrogels," wherein the pressure-sensitive adhesive property is achieved by plasticization of a polymer with water and/or a hydrophilic plasticizer. Such pressure sensitive adhesive compositions may contain active ingredients that are present in a free state or complexed with the cyclodextrin molecules contained therein. Per Lipman, a "cyclodextrin containing hydrocolloid adhesive" can be made by dry mixing components to form hydrogels and pressing them into sheets. When desired, actives may be added to the dry mix when making exemplary hydrogels.

U.S. Pat. No. 4,538,603 to Pawelchuck describes wound dressings the have an adhesive layer that is placed in contact with a wound and surrounding normal skin. The adhesive layer comprises a homogeneous blend of one or more pressure sensitive adhesive materials, one or more water dispersible hydrocolloidal materials, a tackifier and a plasticizer or solvent. The water dispersible hydrocolloids are described as providing wet tack for the adhesive layer of the wound dressings. The wound dressings are made by forming a homogeneous dispersion of a pressure sensitive adhesive material and any thermoplastic elastomer with a heavy duty mixer, e.g., a kneader mixer or sigma blade mixer. The hydrocolloid gums, water swellable cohesive strengthening agents, hydratable polymers and any other optional ingredients are added and mixing is continued until a homogeneous dough is formed. The dough is extruded into a thick slab which is thinned using pressure rollers to the desired thickness to form a dressing. Small amounts of a pharmacologically active ingredient can be included in the adhesive layer, including, for example, an antibiotic or an antimicrobial agent such as neomycin, an antiseptic agent such as povidone iodine, and an anti-inflammatory agent such as hydrocortisone or triamcinolone acetonide.

U.S. 2017/0304215 to Frezza describes a medicated hydrocolloid dressing that forms a component of acne treatment dressings. The hydrocolloid dressings are described as a hi-tack dressing, which can comprise a hydrophobic pressure sensitive adhesive (e.g., butyl rubber or a styrene-isoprene-styrene (SIS) block copolymer) compounded with hydrophilic particulates. The hydrocolloid dressing is said to form a gel in the presence of water. The hydrocolloid dressing may be made by providing a solution of an active agent such as salicylic acid, benzoyl peroxide and sulfur, and mixing the solution of the active agent with a paste comprising hydrocolloid components to form a mixture. The mixture is applied to a removable layer to generate the medicated hydrocolloid dressing. It is said that the acne agent is present in the hydrocolloid dressing at an amount so as to not reduce the absorption capability of the hydrocolloid dressing. Active agents can be associated with the hydrocolloid dressing by being dispersed within the hydrocolloid dressing, coated on the hydrocolloid dressing, co-mixed with the components of the hydrocolloid dressing, or otherwise physically contacted with the hydrocolloid dressing so that the dressing and the active agent do not separate from one another until the dressing is applied to skin surface.

A need remains for hydrocolloid dressings that contain active agents homogeneously distributed therein and methods of making the same. It would be desirable for such hydrocolloid dressings to deliver actives to skin over time, as fluids from the skin are absorbed by the hydrocolloid dressings. It would further be desirable if such hydrocolloid dressings were substantially free of components, for example water and/or cyclodextrin, that may encourage microbial growth. It would further be desirable for there to be a method of making such hydrocolloid dressings such that the active agents are encapsulated within the hydrocolloid dressing, without having to separately source or make encapsulated actives that are compatible with other components of the hydrocolloid dressing and remain stable therein.

While a variety of hydrocolloid dressings have been made and used, it is believed that no one prior to the inventors has made or used an invention as described herein.

BRIEF SUMMARY

In general, the present disclosure is directed to anhydrous hydrocolloid dressings comprising encapsulated therapeutic agents that are homogeneously distributed therein, and methods of making the same. The present disclosure is further directed to acne treatment dressings comprising exemplary anhydrous hydrocolloid matrices.

Exemplary anhydrous hydrocolloid matrices comprise one or more encapsulated therapeutic agents. Each of the one or more encapsulated therapeutic agents is encapsulated by encapsulating agents comprising a viscosity modifier, a hydrocarbon emollient; and bulk components of the anhydrous hydrocolloid matrix. The one or more encapsulated therapeutic agents are homogeneously distributed in the anhydrous hydrocolloid matrix.

Exemplary acne treatment dressings comprising a laminate of a water impermeable or semi-water impermeable backing, a release liner; and an exemplary anhydrous hydrocolloid matrix. The anhydrous hydrocolloid matrix is disposed between the backing and the release liner.

Exemplary methods of making an anhydrous hydrocolloid matrix premix, comprise mixing together to form a mixture: encapsulating agents comprising viscosity modifiers and hydrocarbon emollients, and at least one or more therapeutic agents selected from: an acne agent; a skin conditioning agent; and combinations thereof. Exemplary methods further comprise high shear mixing the mixture to form the premix, wherein the premix comprises the at least one or more therapeutic agents homogenously distributed therein. Exemplary methods further comprise mixing the premix with bulk components of an anhydrous hydrocolloid matrix until an anhydrous hydrocolloid matrix comprising the at least one or more encapsulated therapeutic agents are homogeneously distributed therein.

BRIEF DESCRIPTION OF THE DRAWINGS

It is believed the present invention will be better understood from the following description of certain examples taken in conjunction with the accompanying drawings.

The drawings are not intended to be limiting in any way, and it is contemplated that various embodiments of the invention may be carried out in a variety of other ways, including those not necessarily depicted in the drawing. The accompanying drawing that is incorporated in and forms a part of the specification illustrates several aspects of the present invention, and together with the description serves to explain the principles of the invention.

DETAILED DESCRIPTION

The following description of certain examples of the invention should not be used to limit the scope of the present invention. Other examples, features, aspects, embodiments and advantages of the invention will become apparent to those of ordinary skill in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9 and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

Unless otherwise noted herein, terms are to be understood according to conventional usage by those of ordinary skill in the relevant art. In case of conflict, the present document, including definitions, will control. Preferred methods and materials are described below, although methods and materials similar or equivalent to those described herein may be used in practice or testing of the present invention. The materials, methods and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those of ordinary skill in the art, and so forth.

"About" or "approximately" as used herein, means within an acceptable error range for the particular value as determined by one of ordinary skill in the art, which will depend in part on how the value is measured or determined, e.g., the limitations of the measurement system. For example, "about" may mean a range of up to 20%, or up to 10%, or up to 5%, or up to 1% of a particular value. Where particular values are described in the application and claims, unless otherwise stated the term "about" meaning within an acceptable error range for the particular value should be assumed.

"Acne" as used herein means a disease involving the oil glands and hair follicles of the skin which is manifested by blackheads, whiteheads, acne pimples, acne blemishes, cystic acne and combinations thereof.

"Acne agent" as used herein, means an active agent for use in the treatment of acne and/or acne blemishes.

"Acne blemish" as used herein, means a flaw in the skin resulting from acne.

"Anhydrous" as used herein, means having a water activity of less than or equal to 0.75 $a_w$, as defined in United States Pharmacopeial Convention, Incorporated ("USP") USP-NF 1112—"Application of Water Activity Determination to Nonsterile Pharmaceutical Products."

"Bulk component(s)" as used herein, means components in an anhydrous hydrocolloid matrix exclusive of components in a "premix" as described herein.

"Comprising" as used herein, means that the various components or steps, can be conjointly employed in practicing the present invention. Accordingly, the term "comprising" encompasses the more restrictive terms "consisting essentially of" and "consisting of."

"Encapsulated" as used herein, means to be encased, as if, but not actually in, a capsule.

"Encapsulated active" as used herein, means an active agent that is encapsulated by components of a premix, and in some contexts as described herein, further encapsulated by bulk components of a hydrocolloid matrix as described herein.

"Homogeneously distributed" as used herein relates to one or more therapeutic agents (e.g., one or more acne agent(s), skin conditioning agent(s) and combinations thereof) that are present in an anhydrous hydrocolloid matrix. Such one or more therapeutic agents are "homogeneously distributed" within an exemplary anhydrous hydrocolloid matrix when they are distributed evenly throughout the anhydrous hydrocolloid matrix, such that they would deliver to skin a safe and consistent amount of the one or more therapeutic agent(s) that are present in any sample taken from within the anhydrous hydrocolloid matrix (i.e., the therapeutic agents do not clump together and form hot spots). Such "homogenous distribution" can be seen microscopically, but may also quantified using high performance liquid chromatography (i.e., "HPLC").

"Natural" as used herein, refers to a chemical compound that can occur in nature, as opposed to only being man-made, such as through chemical synthesis.

"One or more encapsulated therapeutic agents" as used herein, means that a single therapeutic agent (for example, salicylic acid) may be encapsulated in a given anhydrous hydrocolloid matrix or two or more different therapeutic agents (for example, salicylic acid, squalane and petrolatum) may be encapsulated in a given anhydrous hydrocolloid matrix.

"Substantially Free" is used interchangeably herein with "substantially free" as used herein, means no effective amount of a specified component or a specified class of components, or about 1 wt. % or less, about 0.1 wt. % or less, or even about 0.01 wt. % or less, or 0% (i.e., completely free).

"Therapeutic" as used therein, means treating or curing of a disease and/or condition.

As used herein, "therapeutic agent" means a substance that treats and/or cures a disease or condition.

As described above, known hydrocolloid and hydrogel dressings are typically made by dry mixing the bulk components of a hydrocolloid or hydrogel together to form a dry powder mix or a paste, to which powdered and/or liquid active(s) are added and mixed. The resulting mixtures are extruded into dressings and/or applied to a backing to form dressings. Hydrocolloids and hydrogels containing active ingredients made in this way have been incorporated into a variety of medicated dressings, including acne treatment dressings.

Without wishing to be bound by theory, it is believed that mixing dry and/or liquid actives into a dry mix of the bulk ingredients of a hydrocolloid or hydrogel, results in hydrocolloids or hydrogels in which the actives are embedded in the resulting matrices, and as such, they are not evenly dispersed therein and can even be "clumped together." As such, active "hot spots" may be present in dressings made from hydrocolloids or hydrogels that have been made in this way. It is further believed that an uneven distribution of actives in hydrocolloid or hydrogel dressings can result in inconsistent delivery of actives to the skin over time. It is also believed that a release of a high load of active(s) from active hot spots onto skin within a short period of time (or all at once) results in yet further irritation of a consumer's skin, adding to a consumer's perception of harm and/or aversion to pain. This can be especially true when the actives that are delivered are acne agents, which are known to be irritating to the skin. Thus, uncontrolled release of active agents, particularly acne agents to the skin, may prompt a consumer to prematurely cease a course of treatment, particularly acne treatment, and in some circumstances, forgo any further use of a medicated treatment dressing, particularly, an acne treatment dressing. Moreover, delivery of high doses of acne agents all at once, may run afoul of certain regulatory requirements.

The present disclosure relates to new methods of making active-containing anhydrous hydrocolloid matrices. Using the new methods, therapeutic agent(s) are encapsulated by encapsulating agents to form exemplary premixes. When exemplary premixes are added to bulk components of a hydrocolloid matrix, the encapsulated active(s) in the premix are further encapsulated by the bulk components of the hydrocolloid matrix.

By using the methods described herein, exemplary anhydrous hydrocolloid matrices comprising encapsulated therapeutic agent(s) that are homogeneously distributed therein may be made. As such, exemplary anhydrous hydrocolloid matrices are characterized by several advantages over known active-containing hydrocolloid and hydrogel matrices, as well as over dressings into which they may be incorporated; some, but not all, of the advantages are described hereinbelow.

A first advantage is that encapsulated therapeutic agent(s) in exemplary anhydrous hydrocolloid matrices are protected from being destabilized by bulk components in a hydrocolloid matrix and/or from being destabilized by environmental factors (e.g., oxidized). This advantage may eliminate the expense and time associated with having to otherwise source premade and/or to otherwise pre-make active-containing capsules and having to add them to the bulk components of a hydrocolloid matrix, particularly in such a way that the active-containing capsules are homogeneously distributed therein without being ruptured.

A further advantage is that by virtue of being homogenously distributed in exemplary anhydrous hydrocolloid matrices, active "hot spots" can be avoided. This advantage sets exemplary anhydrous hydrocolloid matrices apart from known hydrocolloid and hydrogel matrices, that contain active(s) that are unevenly distributed therein, particularly as a result of adding the active(s) into a dry mix of bulk components as is known in the art. As noted above, such known hydrocolloid and hydrogel matrices can be characterized by inconsistent delivery of active(s) to the skin over time, since the active(s) are unevenly distributed in the matrices, and can even be clumped together in active hot spots.

A further advantage of exemplary anhydrous hydrocolloid matrices is evident when they are used alone, or as a part of an acne treatment dressing including, but not limited to the ones described in U.S. 2017/0304215 to Frezza, to treat an acne blemish. After an exemplary anhydrous hydrocolloid matrix is applied to an acne blemish, aqueous fluids from the acne blemish are absorbed into the anhydrous hydrocolloid matrix. As fluids are absorbed, therapeutic agent(s) that are homogeneously distributed in an exemplary anhydrous hydrocolloid matrix are released to the acne blemish. It is believed that as additional fluids are absorbed by the anhydrous hydrocolloid matrix, additional therapeutic agent(s) are released. Thus, while an exemplary anhydrous hydrocolloid matrix remains on the skin, it may deliver the therapeutic agent payload present therein over a period of time to the acne (and any surrounding skin), resulting in an "extended release" of the therapeutic agent(s) into the acne blemish. Extending release of therapeutic agent(s) may result in an even dosing of acne and surrounding skin, with therapeutic agent(s) over time, instead of all at once. Accordingly, acne may be treated and/or benefits to the skin delivered, while reducing or eliminating irritating side effects, which can in turn prompt a consumer to prematurely cease use and/or refrain from a repurchase. Moreover, regulatory requirements for dosing rates of active agents to the skin may be met.

A further advantage of exemplary anhydrous hydrocolloid matrices is that their anhydrous nature prevents microbial growth that can otherwise occur when known hydrocolloid and hydrogel dressings comprising aqueous component(s) are made or used without first being subjected to sterilization.

A further advantage of some exemplary anhydrous hydrocolloid matrices is that in addition to being anhydrous, they are also substantially free of one or more cyclodextrins. Cyclodextrins are a type of sugar. Without wishing to be bound by theory, it is believed that the presence of cyclodextrins (and/or other sugar(s)) in known hydrocolloid or hydrogel matrices, may favor microbial growth. Thus, since some, if not all, of the exemplary anhydrous hydrocolloid matrices and dressings that comprise them, are substantially free of cyclodextrin (or any other sugars), and as such, a need to sterilize them prior to use, as is typical in the art, is further eliminated.

These and other features of the disclosed methods and exemplary anhydrous hydrocolloid matrices are described hereinbelow.

Premix Compositions

Exemplary anhydrous hydrocolloid matrices comprising encapsulated therapeutic agent(s) are made by making a premix containing one or more therapeutic agent(s) and blending the premix with bulk components of the hydrocolloid matrix. Without wishing to be bound by theory, it is believed that as an exemplary premix is being made as described herein, therapeutic agent(s) are encapsulated by other agents in the premix, i.e., "encapsulating agents," and the encapsulated therapeutic agent(s) are homogeneously distributed within the premix. Exemplary premixes comprise encapsulating agents, which in turn comprise: (A) viscosity modifier; and (B) hydrocarbon emollient. Exemplary premixes further comprise (C) therapeutic agent.

(A) Viscosity Modifier:

Exemplary premixes comprise one or more viscosity modifiers that act as encapsulating agents in the premixes. Exemplary viscosity modifiers of use include those that are typically be found in anhydrous systems. Viscosity modifiers may be film-forming, act as a tackifier, act as a gelling agent and combinations thereof.

Exemplary viscosity modifiers of use may be selected from: natural hydrophilic polymers; synthetic hydrophilic polymers; and combinations thereof. Exemplary natural hydrophilic polymers of use may be selected from: celluloses; gums; chitosan; alginates; agars; gelatin; pectin; resins; and combinations thereof. Exemplary synthetic hydrophilic polymers of use may be selected from: polyisobutylene; block copolymers; and combinations thereof. Exemplary block copolymers include those that are known in the art of hydrophobic pressure sensitive adhesives. Some exemplary premixes comprise copolymers selected from: styrene-olefin-styrene copolymers; styrene-isoprene-styrene copolymers; and combinations thereof.

Exemplary premixes may comprise a total of from about 1% to about 5%, from about 1.5% to about 4.5% or from about 2% to about 4% of one or more viscosity modifiers, by weight of the premix.

(B) Hydrocarbon Emollient:

Exemplary premixes comprise one or more hydrocarbon emollients that act as encapsulating agents in exemplary premixes. Exemplary hydrocarbon emollients of use are compounds carrying only carbon and hydrogen groups, including groups selected from: aliphatic groups; cyclic groups; and combinations thereof. Exemplary hydrocarbon emollients of use may be selected from: aliphatic hydrocarbons; cyclic hydrocarbons; and mixtures thereof. Exemplary aliphatic hydrocarbons of us may be selected from: liquid paraffin; dodecane; isododecane; isohexadecane; isoeicosane; petrolatum; microcrystalline wax; polyethylene; squalene, squalane; aliphatic hydrocarbons with monocarboxylic acid groups; and mixtures thereof. Exemplary aliphatic hydrocarbons with monocarboxylic acid groups of use may be present in oils selected from: sunflower oil; safflower oil; palm oil; jojoba oil; castor oil; and mixtures thereof. Exemplary cyclic hydrocarbons of use may be selected from: terpenes; cyclohexasiloxane; cyclopentasiloxane; and combinations thereof.

Hydrocarbon emollients may have a dual function of coating therapeutic agent(s) in an exemplary premix and acting as skin conditioning agent when a resulting anhydrous hydrocolloid matrix is applied to skin. For the purposes of the present disclosure, the total weight percentages of hydrocarbon emollients that may be present in exemplary premixes, do not include weight percentages of hydrocarbon emollients that only act as skin conditioning agents (i.e., that do not have the function of encapsulating actives).

Exemplary premixes may comprise a total of from about 3% to about 8%, from about 3.5% to about 7.5% or from about 4.5% to about 7% of one or more hydrocarbon emollients, by weight of the premix.

(C) Therapeutic Agent:

Exemplary premixes comprise at least one therapeutic agent selected from: an acne agent; a skin conditioning agent; and combinations thereof. The amount of therapeutic agent that is included in an exemplary premix can be determined by one of ordinary skill in the art, based upon the total amount of therapeutic agent that is to be present in a finished anhydrous hydrocolloid matrix that is made using the premix.

Some exemplary premixes comprise a single acne agent, and other exemplary premixes, comprise more than one acne agent, e.g., 2, 3, 4, 5, etc., acne agents. Exemplary acne agents of use in premixes may be selected from: salicylic acid; resourcinol; resourcinol monoacetate; sulfur; and combinations thereof. Some exemplary premixes comprise acne agents selected from: salicylic acid; resourcinol; resourcinol monoacetate; sulfur; and combinations thereof.

Exemplary anhydrous hydrocolloid matrices that are made with exemplary premixes may comprise a total amount of at least one therapeutic agent that is present at from about 0.5% to about 16% by weight percentage of only the anhydrous hydrocolloid matrix in which they are homogeneously distributed. Some exemplary anhydrous hydrocolloid matrices comprise a total amount of at least one therapeutic agent in an amount of: from about 0.5% to about 15%; from about 0.5% to about 14%; from about 0.5% to about 13%; from about 0.5% to about 12%; from about 0.5% to about 11%; from about 0.5% to about 10%; from about 0.5% to about 9%; from about 0.5% to about 8%; from about 0.5% to about 7%; from about 0.5% to about 6%; from about 0.5% to about 5%; from about 0.5% to about 4%; from about 0.5% to about 3%; from about 0.5% to about 2%; from about 0.5% to about 1.9%; from about 0.5% to about 1.8%; from about 0.5% to about 1.7%; from about 0.5% to about 1.6%; from about 0.5% to about 1.5%; from about 0.5% to about 1.4%; from about 0.5% to about 1.3%; from about 0.5% to about 1.2%; from about 0.5% to about 1.1%; from about 0.5% to about 1.0%; from about 0.5% to about 0.9%; from about 0.5% to about 0.8%; from about 0.5% to about 0.7%; or from about 0.5% to about 0.6%; about 0.4%; by weight of only the anhydrous hydrocolloid matrix in which they are homogeneously distributed.

Some exemplary anhydrous hydrocolloid matrices comprise a total amount of at least one therapeutic agent of: about 0.45%; about 0.5%; about 0.6%; about 0.7%; about 0.8%; about 0.9%; about 1.0%; about 1.1%; about 1.2%; about 1.3%; about 1.4%; about 1.5%; about 1.6%; about 1.7%; about 1.8%; about 1.9%; about 2.0%; about 2.2%; about 2.4%; or about 2.5%; by weight of only the anhydrous hydrocolloid matrix in which they are homogeneously distributed.

Some exemplary anhydrous hydrocolloid matrices that are made with exemplary premixes may comprise a total amount of salicylic acid that is present in a weight percentage of: from about 0.5% to about 2%; from about 0.5% to about 1.5%; from about 0.5%, about 0.6; from 0.7% to about 0.8%; by weight of only the anhydrous hydrocolloid matrix in which they are homogeneously distributed.

In some exemplary anhydrous hydrocolloid matrices, the at least one acne agent is or comprises salicylic acid that is present in the anhydrous hydrocolloid matrices at an amount of: about 0.5%, 0.9%; about 1.0%; about 1.1%; about 1.2%; about 1.3%; about 1.4%; about 1.5%; about 1.6%; about 1.7%; about 1.8%; about 1.9%; or about 2.0%; by weight of only the anhydrous hydrocolloid matrix in which it is homogeneously distributed.

In some exemplary anhydrous hydrocolloid matrices that are made with exemplary premixes the at least one acne agent is or comprises sulfur, that is present in exemplary anhydrous hydrocolloid matrices at weight percentage of: from about 2% to about 10%; from about 3% to about 9%; from about 3% to about 8%; from about 3% to about 7%; from about 3% to about 6%; from about 3% to about 5%; or from about 3% to about 4%; by weight of only the anhydrous hydrocolloid matrix in which it is homogeneously distributed.

In some exemplary anhydrous hydrocolloid matrices, the at least one acne agent is a combination of resorcinol 2 percent in combination with sulfur or resorcinol monoacetate that is present in exemplary anhydrous hydrocolloid matrices at weight percentage of: about 1% to about 5%; or about 1% to about 4%; about 1% to about 3%; or about 1%; about 2%; about 3%; about 4% or about 5%; by weight of only the anhydrous hydrocolloid matrix in which it is homogeneously distributed. In some exemplary anhydrous hydrocolloid matrices, resorcinol monoacetate is present at an amount of about 1% to about 5%; or about 1% to about 4%; about 2% to about 4%; or about 1%; about 2%; about 3%; about 4%; or about 5%. In exemplary anhydrous hydrocolloid matrices in which resorcinol or resorcinol monoacetate are utilized, the amount of sulfur that is present by weight of the anhydrous hydrocolloid matrix in which it is homogeneously distributed, may be present at from: about 3% to about 8%; about 3% to about 7%; about 3% to about 6%; about 3% to about 5%; or about 3% to about 4%; by weight of only the anhydrous hydrocolloid matrix in which they are homogeneously distributed.

Amounts and combinations of acne agents of use include those that conform with local governmental regulations and laws. For example, exemplary amounts and combinations of acne agents(s) include those that are described in Part 333.320 of Title 21 in the U.S. Code of Federal Regulations, which are set forth below in Table 1. For the purposes of this disclosure, the weight percentages of acne agent(s) that are set forth in Table 1 are total weight percentages of the active(s) by weight of only the anhydrous hydrocolloid matrix in which the active(s) are homogeneously distributed (i.e., the weight percentages that are set forth do not include the weights of any other components (e.g., a backing, a liner, etc.) that may also form parts of exemplary acne treatment dressings).

TABLE 1

Acne Agent(s) by Weight Percentage of Exemplary Acne Treatment Dressings (a) Resorcinol, 2 percent, when combined with sulfur
(b) Resorcinol monoacetate, 3 percent, when combined with sulfur
(c) Salicylic acid, 0.5 to 2 percent
(d) Sulfur, 3 to 10 percent
(e) Sulfur, 3 to 8 percent, when combined with resorcinol or resorcinol monoacetate Exemplary skin conditioning agents of use include those that act as: emollients; keratolytic agents; anti-inflammatory agents; anti-bacterial agents; and combinations thereof. For the purposes of this disclosure, it is noted that hydrocarbon emollients may serve a dual purpose of providing skin care benefits as well as functioning to encapsulate actives. It is further noted that the purposes of the present disclosure, the total weight percentages of hydrocarbon emollients that are disclosed, do not include weight percentages of hydrocarbon emollients that are present in exemplary premixes solely to serve as skin conditioning agents (i.e., that do not also act as encapsulating agents).

Additional/alternative exemplary skin conditioning agents may be selected from: polysaccharides; fatty acids; esters of fatty acids; tartrates; dicarboxylic acids; glycols; organic acids; and combinations thereof.

Exemplary emollients of use as skin conditioning agents that are encapsulated as described herein may be selected from: vitamin A; safflower oil; squalane; argan oil; derivatives of any one of the foregoing; and combinations thereof.

Exemplary keratolytic agents of use may be selected from: retinoids; allantoin; urea; alpha-hydroxy acids; beta-hydroxy acids; salicylic acid; enzymes; derivatives of any one of the foregoing; and combinations thereof.

Exemplary anti-inflammatory agents of use may be selected from: vitamin E; amino acids; *Saccharomyces* ferment; oat; alpha-bisabolol; aloe; horse chestnut; licorice root; chamomile; derivatives of any one of the foregoing; and combinations thereof.

Exemplary anti-bacterial agents of use may be selected from: acne agents; ferments; botanicals; *Leptospernum scoparium* oil; citrus paradisi seed; magnolol; honokiol; derivatives of any one of the foregoing; and combinations thereof.

In addition to comprising one or more encapsulated therapeutic agents, some exemplary anhydrous hydrocolloid matrices further comprise one or more therapeutic agents that are associated with the anhydrous hydrocolloid matrices after it has been made. For example, one or more therapeutic agents may be coated upon and/or sprayed upon one or more surfaces of the anhydrous hydrocolloid matrix, and/or otherwise physically contacted therewith so that the resulting dressing and the active agent that is applied, do not separate from one another until the dressing is applied to skin surface. For the purposes if this disclosure, weight percentages of therapeutic agents that are added to exemplary anhydrous hydrocolloid matrices after they have been made are not included in the disclosed weight percentages of therapeutic agents in the exemplary anhydrous hydrocolloid matrices.

Method of Making Premixes

An exemplary method of making a premix comprises: (a) mixing together at ambient temperature (e.g., from about 15° C. to about 30° C.) at least one or more therapeutic agents with encapsulating agents comprising viscosity modifiers and hydrocarbon emollients to form a mixture; and (b) high shear mixing the mixture to form the premix, wherein the premix comprises encapsulated therapeutic agents having the desired particle size distribution and being homogenously distributed in the premix.

Without wishing to be bound by theory, it is believed that when a premix is made using an exemplary method, the encapsulating agents, i.e., the viscosity modifier(s) and hydrocarbon emollient(s) encapsulate the therapeutic agent(s) as they are homogeneously distributed and micronized during high shear mixing.

Method of Making an Anhydrous Hydrocolloid Matrix

Once an exemplary premix is made, it can be mixed (e.g., with a paddle mixer) into bulk components of an anhydrous hydrocolloid matrix. Bulk components of use include those components that are known in the art for being of use in anhydrous hydrocolloid matrices. Mixing continues until a homogenous anhydrous hydrocolloid matrix comprising encapsulated therapeutic agent(s) homogeneously dispersed therein is made.

Without wishing to be bound by theory, it is believed that when the encapsulated therapeutic agent(s) in the premix are mixed with the bulk components of an anhydrous hydrocolloid matrix, the encapsulated therapeutic agents are coated yet again by bulk components of the anhydrous hydrocolloid matrix. As such, exemplary anhydrous hydrocolloid matrices comprise therapeutic agent(s) homogeneously distributed therein, wherein the therapeutic agent(s) are encapsulated twice, having at least two layers of protection from other elements in the matrices and/or from destabilizing elements in the environment.

Exemplary bulk components of an anhydrous hydrocolloid matrix include those that are described in U.S. 2017/0304215 to Frezza. Exemplary bulk components may comprise some of the same components that are found in exemplary premixes. For example, bulk components may also include: (A) viscosity modifier and (B) hydrocarbon emollient.

For the purposes of the present disclosure, exemplary anhydrous hydrocolloid matrices comprising encapsulated therapeutic agent(s) homogeneously distributed therein, may comprise by weight percentage of the resulting matrices, a total amount of components (A) and (B), wherein the total amount of each of these components includes the amount of that component that was present in the premix in addition to the total amount of that component that was present in the bulk components of the anhydrous hydrocolloid matrix. For example, some exemplary anhydrous hydrocolloid matrices may comprise: (A) a total of from about 10% to about 40%, from about 12% to about 37%, or from about 15% to about 35% of any one or more of viscosity modifiers, by weight percentage of the anhydrous hydrocolloid matrices; and (B) a total of from about from about 25% to about 60%, from about 27% to about 55%, or from about 30% to about 50%, of any one or more hydrocarbon emollients, by weight percentage of the anhydrous hydrocolloid matrices.

Bulk components of some exemplary anhydrous hydrocolloid matrices may further comprise stability enhancers. Exemplary stability enhancers of use may be selected from: antioxidants; antimicrobials; and mixtures thereof.

Exemplary antioxidants of use may be selected from: pentaerythrityl tetra-di-t-butyl hydroxyhydrocinnamate; phenols; esters; cinnamate tetraesters; hydroxycinnamic acid; ubiquinone; tocopherol; tocopheryl acetate; tetrahexyldecyl ascorbate; bis-ethylhexyl hydroxydimethoxy benzylmalonate; ferulic acid; derivatives of any one of the foregoing; and mixtures thereof.

Exemplary antimicrobials of use may be selected from: benzoquinones; quaternary ammonium compounds; parabens; sodium metabisulfite; sulfur dioxide; sorbic acid; sorbates; benzoic acid; benzoates; butylated hydroxytoluene (BHT); butylated hydroxyanisole; benzaldehyde; essential oils; botanicals; propionic acid; derivatives of any of the foregoing; and mixtures thereof.

Some exemplary anhydrous hydrocolloid matrices comprising therapeutic agent(s) homogeneously distributed therein may comprise a total of from about 0.01% to about 5%, from about 0.1% to about 3%, or from about 0.5% to about 2%, of any one or more stability enhancer(s), by weight percentage of the anhydrous hydrocolloid matrices.

Method of Making an Acne Dressing

Once an exemplary anhydrous hydrocolloid matrix comprising encapsulated therapeutic agents homogenously distributed therein is made, it can be formed into an acne treatment dressing using methods that are known in the art including, but not limited to, the methods that are described in U.S. 2017/0304215 to Frezza.

Exemplary acne treatment dressings may consist of exemplary anhydrous hydrocolloid matrices or they may further comprise other components as is known in the art. Regardless, the exemplary anhydrous hydrocolloid matrices may be formed into a flexible and substantially planar, dressing, i.e., they may be formed into a flexible therapeutic body. For example, a flexible therapeutic body may be formed by laminating an exemplary anhydrous hydrocolloid matrix between a water impermeable or semi-water impermeable backing and a release liner. The thickness, size and shape of a resulting acne treatment dressing may be customized for a targeted treatment area of the skin, as is known to one of ordinary skill in the art.

Figure 1:
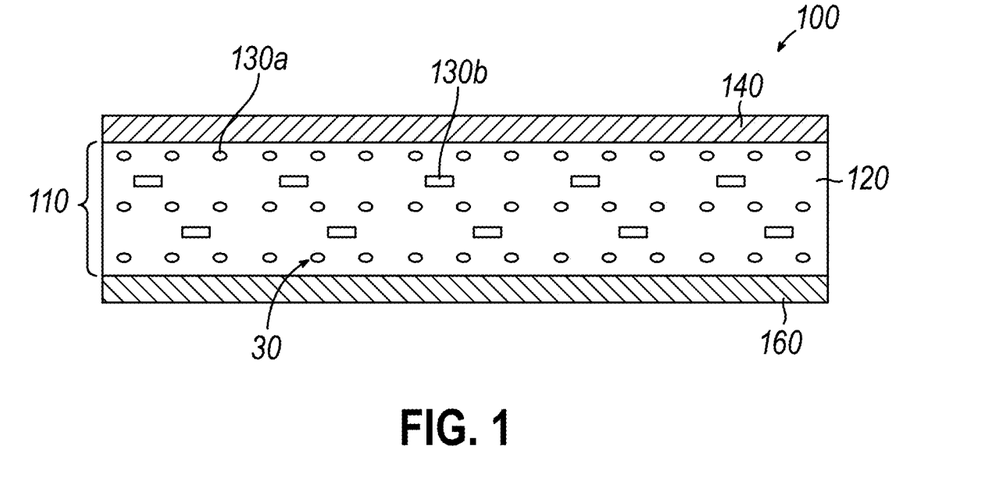
FIG. 1 shows a cross-sectional view of a first exemplary acne treatment dressing comprising an exemplary anhydrous hydrocolloid matrix comprising encapsulated therapeutic agent(s) homogeneously distributed therein.
Figure 2:
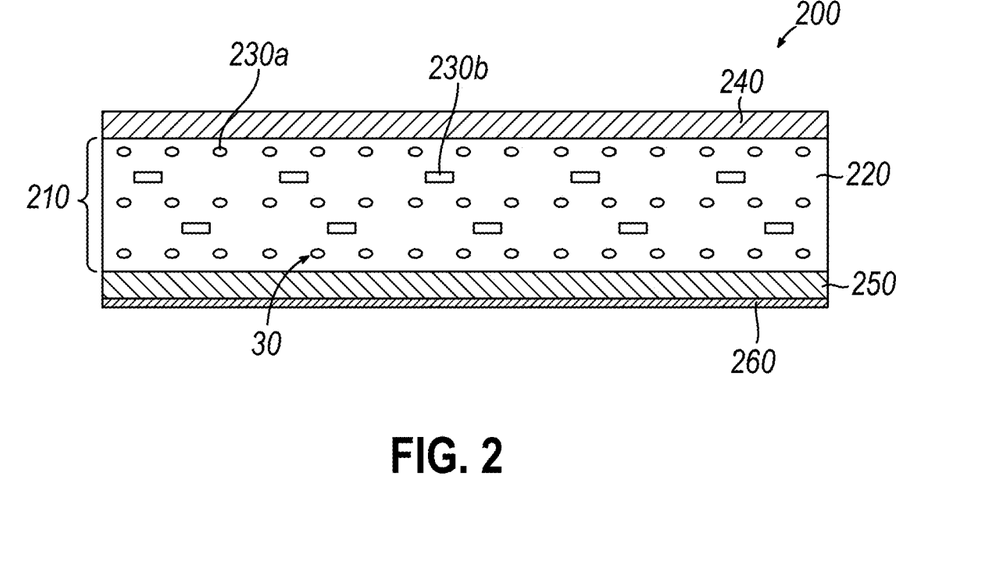
FIG. 2 shows a cross-sectional view of a second exemplary acne treatment dressing comprising an exemplary anhydrous hydrocolloid matrix comprising encapsulated therapeutic agent(s) homogeneously distributed therein.

Referencing FIGS. 1 and 2, exemplary acne treatment patches (100, 200) comprise a substantially planar therapeutic body (110, 210) including an exemplary anhydrous hydrocolloid matrix (120, 220) and encapsulated therapeutic agent(s) (130*a*, 130*b*, 230*a*, 230*b*) homogeneously distributed in each anhydrous hydrocolloid matrix. Referencing FIG. 1, a first exemplary acne treatment patch (100) further comprises: a first water impermeable or water semi-impermeable layer (140) that is disposed on a first side of the therapeutic body (110); and a second layer (160) is located on a second side of the therapeutic body (110), wherein the second layer is a liner layer (160) that is removable from the therapeutic body (110), prior to application of the acne treatment patch acne (100) to acne (310) on a face of a consumer (300), as is shown for example, in FIG. 3.

Figure 3:
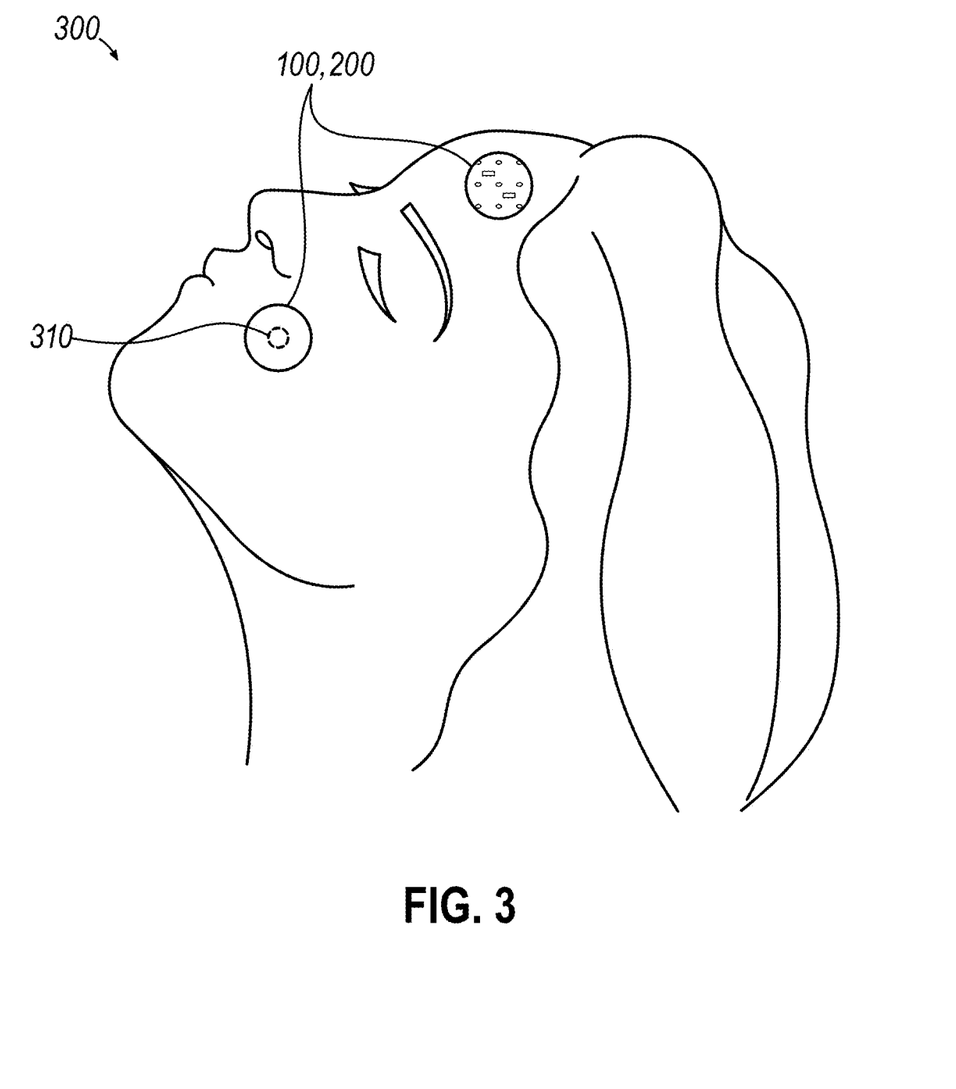
FIG. 3 shows exemplary acne treatment patches applied to skin.

Referencing FIG. 2, a second exemplary acne treatment patch (200) comprises a first water impermeable or water semi-impermeable layer (240) that is disposed on a first side of the therapeutic body (210); an adhesive layer (250) is disposed on a second side of the therapeutic body (210); and a further layer that is a liner layer (260) that is removable from the therapeutic body (210), prior to application of the acne treatment patch acne (200) to acne (310) on a face of a consumer (300), as is shown for example, in FIG. 3.

Methods of Use

Methods of treating acne include, but are not limited to, those that are set forth in U.S. 20170304215A1 to Frezza. Exemplary methods include providing an acne treatment dressing as described herein. The exemplary methods may comprise cleaning the skin surface is cleaned (e.g., using soap and/or water, or a suitable cleansing solution or agent) prior to applying the dressing. Further comprise applying the dressing to a skin surface, the dressing at least partially covering an acne blemish, and maintaining the dressing on the skin surface for a period of at least 1 hour, thereby treating the acne. In some exemplary methods, the dressing is maintained on the skin surface for a period of at least 6 hours, and this can be repeated daily for a period of at least 3 days.

In some exemplary methods, the period that a dressing is maintained on a skin surface can be as little as 10-15 minutes, but is suitably at least 1 hour, including maintaining the device on a skin surface for at least 6 hours (e.g., overnight) up to an including 12-24 hours.

Suitable skin surfaces onto which the devices can be applied include any surface where an acne occurs, including for example, the face, neck, back, shoulders, chest, buttocks, trunk, legs, etc. Suitably, the devices and methods described herein are useful in the treatment of acne in mammals, and specifically humans.

In exemplary methods of treatment described herein, the treatment is suitably repeated on a daily basis, though can be repeated on semi-daily (i.e., every 2, 3, 4, 5 days) etc., as desired. Suitably, the treatment is repeated daily for at least 3 days, or until the acne blemish is no longer noticeable to a user. The methods can be repeated for at least 3-30 days, e.g., about 7-14 days, or about 7-10 days.

In embodiments in which a liner layer (160, 260) is included on an inner surface of the device, the methods further comprise removing the removable layer prior to applying the device (100, 200) to a skin surface (300).

In some exemplary methods, after the liner layer (160, 260) is removed from an individual dressing (100, 200), prior to applying to skin surface. Referencing FIG. 3, a liner layer (160, 260) has been removed from an individual dressing (100, 200), leaving behind the remaining portions of the dressing on the skin surface (300).

As described herein, applying a dressing (100, 200) to a skin surface to at least partially cover (suitably completely cover) acne, allows the hydrocolloid dressing to absorb impurities, including oil, pus, dirt, bacteria, etc., and also allow the active agent (e.g., salicylic acid, sulfur, etc.) to absorb onto the surface of the acne blemish, begin to penetrate the acne blemish, and have a treatment effect on the blemish.

In some exemplary methods a dressing can be removed and replaced immediately, in other exemplary methods, a period of time between removal and replacement is allowed to pass, suitably on the order of 15 minutes to several hours to days, suitably on the order of about 4-18 hours. For example, in some exemplary methods, devices (100, 200) are removed from a skin surface during the day e.g., after waking in the morning, and then reapplied at night, e.g., at bedtime.

Examples and Data

Exemplary anhydrous hydrocolloid matrices with encapsulated therapeutic agent(s) homogeneously distributed therein and having formulas set forth in Table 2, are made using a premix as described above. Weight percentages that are set forth in Table 2 are by weight of the resulting anhydrous hydrocolloid matrices, which include a premix and bulk components of an anhydrous hydrocolloid matrix.

TABLE 2

| Component Type | Component | Ex. 1 Wt % | Ex. 2 Wt % | Ex. 3 Wt % | Ex. 4 Wt % | Ex. 5 Wt % | Ex. 6 Wt % | Ex. 7 Wt % | Ex. 8 Wt % |
|---|---|---|---|---|---|---|---|---|---|
| (A) Viscosity Modifier | Pectin | | | | 2.00 | | 3.00 | | |
| | Gums | | 2.00 | | 3.00 | | 1.00 | 3.00 | |
| | Alginate | 1.00 | | 3.00 | | | | | 1.00 |
| | Agars | | | | | 2.00 | | | 3.00 |
| (B) Hydrocarbon Emollient | Squalane | 3.00 | | 1.00 | 1.00 | | | | |
| | Safflower Oil | | 3.00 | | | | 8.00 | | |
| | Liquid Paraffin | | | 6.00 | | 8.00 | | 3.00 | 4.00 |
| | Petrolatum | 2.00 | | | 3.00 | | | | |
| | Terpenes | | | | | 2.00 | | 3.00 | |
| (C) Therapeutic Agent | | | | | | | | | |
| Acne Agent | Salicylic Acid | 0.50 | | 1.00 | | 1.50 | | 2.00 | |
| | Sulfur | | 3.00 | | 3.00 | | 2.00 | | 10.00 |
| | Resorcinal | | | | 2.00 | | | | |
| | Resorcinol Monoacetate | | | | | | 3.00 | | |

TABLE 2-continued

| Component Type | Component | Ex. 1 Wt % | Ex. 2 Wt % | Ex. 3 Wt % | Ex. 4 Wt % | Ex. 5 Wt % | Ex. 6 Wt % | Ex. 7 Wt % | Ex. 8 Wt % |
|---|---|---|---|---|---|---|---|---|---|
| Skin Conditioning Agent | Aloe Vera | 1.00 | | 2.00 | | | 2.00 | | 0.50 |
| | Allantoin | | 1.00 | | | 2.00 | | 0.50 | |
| | Retinoids | 0.10 | 0.50 | | 0.25 | | | | |
| | Licorice Root | | | | | | 3.00 | | |
| Bulk Components of Anhydrous Hydrocolloid Matrix | | 92.40 | 90.50 | 87.00 | 83.75 | 86.50 | 78.00 | 88.50 | 81.50 |

The resulting anhydrous hydrocolloid matrices are shaped into a flexible therapeutic body and may be used alone as an acne treatment dressing or may be incorporated into an acne treatment dressing comprising other components as described above, using manufacturing methods that are known to one of ordinary skill in the art.

To obtain FDA, OTC and Rx compliance of exemplary acne treatment dressings, it is critical for encapsulated therapeutic agent(s), particularly acne agents(s) to be present in anhydrous hydrocolloid matrices in the intended weight percentages, and for them to be homogeneously distributed within the matrices. Thus, analytical methods of ascertaining acne agent content and distribution must be validated pursuant to established standards. For example, the U.S. Pharmacopeia (USP) defines the requirements that are to be met for analytical methods that are used and relied upon when making, for example, acne treatment dressings. Referencing USP National Formulary 1225 (USP-NF 1225), "Validation of Compendial Procedures" (copyrighted in 2022 by USPC, and incorporated by reference herein) the analytical results must be robust, accurate, precise and meet detection and quantitation limits, among other very specific characteristics, in order for the analytical methods to be used to ensure that exemplary anhydrous hydrocolloid matrices and exemplary acne treatment dressings comprising them comply with the FDA, OTC and Rx requirements in the U.S.

When an anhydrous hydrocolloid matrix which is made with a total of 0.5 wt % of salicylic acid, is assayed for salicylic acid content, a coefficient of variability of equal to or less than +/−10 wt % is presently required to meet FDA, OTC and Rx compliance in the U.S. However, the inventors find that using the current USP-NF Method Standard 43 (Dated May 1, 2020) to measure salicylic acid content by weight percentage of a given exemplary hydrocolloid matrix provides a coefficient of variance of in salicylic acid content, of twice that, or about +/−20%. Such a coefficient of variance is too large to provide a meaningful way to ensure that exemplary hydrocolloid matrices and/or acne treatment dressings comprising them comply with governmental/regulatory standards.

Without wishing to be bound by theory, it is believed that the large variance in salicylic acid content that is observed when using USP-NF Method Standard 43 is attributable to that method having been designed for assaying products that solubilize more readily than the anhydrous hydrocolloid matrices described herein. Thus, the inventor has surprisingly found that a newly discovered or "modified" USP-NF Method Standard 43 ("M-USP-NF MS 43") provides for an assay that not only meets, but exceeds the standards for determining acne agent content in exemplary anhydrous hydrocolloid matrices (that are intended to be used alone an acne treatment dressing and/or that may be incorporated into an acne treatment dressing comprising other components) as set forth in USP National Formulary 1225 (USP-NF 1225), "Validation of Compendial Procedures" (copyrighted in 2022 by USPC). M-USP-NF MS 43 is newly described herein below.

The following assays are undertaken to demonstrate that: (a) exemplary anhydrous hydrocolloid matrices comprise encapsulated salicylic acid at the intended weight percentages; (b) M-USP-NF MS 43 is surprisingly useful for analyzing acne agent content in anhydrous hydrocolloid matrices; and (c) encapsulated salicylic acid is homogeneously distributed in relation to the intended weight percentage of salicylic acid actually being present across multiple batches of exemplary anhydrous hydrocolloid matrices having identical formulations, both prior to and after being made into acne treatment dressing alone and/or in combination with other elements (e.g., backing, liner, etc.).

First, 24 samples of an exemplary anhydrous hydrocolloid matrix comprising an identical formulation that includes a total added weight percentage of 0.6 wt % salicylic acid, are made using the method described herein above.

Second, the salicylic acid content in each of 12 of the samples is measured using USP-NF Method Standard 43 (Dated May 1, 2020) and the results are set forth in Table 3.

TABLE 3

| Batch No. | Salicylic Acid Content (wt %) |
|---|---|
| 1 | 0.60 |
| 2 | 0.50 |
| 3 | 0.50 |
| 4 | 0.40 |
| 5 | 0.60 |
| 6 | 0.58 |
| 7 | 0.60 |
| 8 | 0.55 |
| 9 | 0.49 |
| 10 | 0.56 |
| 11 | 0.42 |
| 12 | 0.42 |
| Mean of 1-12 | 0.52 |
| Standard Deviation | 0.07 |
| Coefficient of Variance (%) | 14 |

As can be seen in Table 3, even though the samples tested are identical and each contain a total added amount of 0.6 wt % salicylic acid, utilizing USP-NF Method Standard 43 (Dated May 1, 2020) to measure the weight percentage of salicylic content provides results as low as 0.42 wt % of salicylic acid and as high as 0.60 wt % salicylic acid and a coefficient of variance of 14.4%. Such results do not meet the standards for analytical results that are set forth in USP National Formulary 1225 (USP-NF 1225), "Validation of Compendial Procedures" (copyrighted in 2022 by USPC). Moreover, these analytical results are not accurate, precise, robust, etc., enough in order to comply with FDA, OTC and Rx requirements in the U.S.

Third, salicylic acid content in each of the other 12 of the samples is measured using M-USP-NF MS 43. M-USP-NF MS 43 comprises all of the steps in USP-NF Method Standard 43 (Dated May 1, 2020), with the following modificatons, newly described herein: (a) heat the anhydrous hydrocolloid matrix back down to a liquid (200-300F) for 30 minutes to spike in active and determine system suitability; (b) dissolve matrix for 24 hours in tetrahydrofuran (THF) until it is finely dispersed and in a homogenous solution; (c) vortex the solution and prepare it for standard HPLC analysis; and (d) sonicate/heat the 6 vials maximum at a time for at least 30 minutes to assure product is 100% in solution. Results are set forth in Table 4.

TABLE 4

| Batch No. | Salicylic Acid Content (wt %) |
|---|---|
| 1 | 0.59 |
| 2 | 0.54 |
| 3 | 0.55 |
| 4 | 0.58 |
| 5 | 0.57 |
| 6 | 0.59 |
| 7 | 0.57 |
| 8 | 0.59 |
| 9 | 0.58 |
| 10 | 0.48 |
| 11 | 0.58 |
| 12 | 0.55 |
| Mean of 1-12 | 0.56 |
| Standard Deviation | 0.03 |
| Coefficient of Variance (%) | 5.6 |

As can be seen in Table 4, by utilizing M-USP-NF MS 43 to analyze salicylic acid content in the 12 identical samples that each are intended to contain a total of 0.6 wt % salicylic acid, provides results as low as 0.48 wt % of salicylic acid and as high as 0.59 wt % salicylic acid and a coefficient of variance of 5.6%. Not only do these results meet the standards for analytical results that are set forth in USP National Formulary 1225 (USP-NF 1225), the coefficient of variance is less than twice that of the analytical results that are otherwise obtained using USP-NF MS 43, without any modifications thereto. Moreover, the coefficient of variance obtained using M-USP-NF MS 43 as newly described herein, not only meets, but significantly exceeds the coefficient of variability of equal to or less than +/−10 wt % that is presently required to meet FDA, OTC and Rx compliance in the U.S.

In light of the foregoing, it is also evident that exemplary methods of making exemplary anhydrous hydrocolloid matrices provide for salicylic acid content that is homogeneous across multiple samples, and as such, can deliver to the skin (either alone or as a part of an acne treatment dressing comprising other components), an intended amount of salicylic acid, which is a safe and effective amount. It can also be seen that salicylic content measured using M-USP-NF MS 43 as newly described herein, is sufficiently accurate and highly reproducible. Moreover, it is believed that these results can be readily extrapolated to include exemplary anhydrous hydrocolloid matrices comprising one or more acne agents in addition to, and/or in lieu of, salicylic acid, as described herein.

M-USP-NF MS 43 may also be used to demonstrate that homogeneity in the intended weight percentage of salicylic acid is maintained across multiple exemplary anhydrous hydrocolloid matrices and/or exemplary acne treatment dressings comprising them, as they are being made. For example, using M-USP-NF MS 43, salicylic acid content is measured at different points during the formation of an exemplary anhydrous hydrocolloid matrix that can be used as an acne treatment dressing alone and/or in combination with other elements (e.g., backing, liner, etc.).

A pre-formed "dough" comprising (A) viscosity modifier(s), (B) therapeutic agent(s) and bulk components of anhydrous hydrocolloid matrix is made using the exemplary method described herein. The dough is pressed through a laminating roll a first time (1), a second time (2) and a third time (3), to generate a laminated sheet. After each time, (1), (2) and (3), the salicylic acid content of a sample of the anhydrous hydrocolloid matrix is measured.

The laminated sheet is then dot rolled (i.e., run through a die and cut into a desired shape). Dot rolling of the laminated sheet can be divided into three time periods: (a) at the beginning of the dot rolling; (b) during the middle of the dot rolling; and at the end of the dot rolling. At the conclusion of each of the time periods, a sample of the dot rolled laminated sheet is measured for salicylic acid content using M-USP-NF MS 43. This entire process is repeated twice for two batches of "dough" that have identical formulations to which a total of 0.6 wt % of salicylic acid has been added, i.e., n=2, and the results are set forth in Table 5.

TABLE 5

| Sample Location* | Salicylic Acid Content (wt %) |
|---|---|
| LR 1 - 1 | 0.5940 |
| LR 1 - 2 | 0.6085 |
| LR 2 - 1 | 0.5966 |
| LR 2 - 2 | 0.6067 |
| LR 3 - 1 | 0.6157 |
| LR 3 -2 | 0.6037 |
| DR - M1 | 0.5946 |
| DR - M2 | 0.5924 |
| DR - B1 | 0.6055 |
| DR - B2 | 0.5928 |
| DR - E1 | 0.6040 |
| DR - E2 | 0.5970 |
| Mean | 0.5997 |
| STD | 0.0068 |
| % CV | 1.1422 |

As can be seen in Table 5, utilizing M-USP-NF MS 43 to analyze salicylic acid content during the processing of the two identical batches of "dough" to which at total of 0.6000 wt % of salicylic acid is added, it is shown that the measured salicylic acid content averages 0.5996+/−0.0069 wt % across both batches of "dough," as well as throughout the process of forming it into an exemplary anhydrous hydrocolloid matrix that can be used as an acne treatment dressing alone and/or in combination with other elements (e.g., backing, liner, etc.). It can further be seen that not only do these results meet the standards for analytical results that are set forth in USP National Formulary 1225 (USP-NF 1225), the coefficient of variance is advantageously almost 20 times less than that of the analytical results that are otherwise obtained using USP-NF MS 43, without any modifications thereto. Moreover, the coefficient of variance obtained using M-USP-NF MS 43 as newly described herein, not only meets, but is advantageously almost 10 times less than the coefficient of variability of equal to or less than +/−10 wt % that is presently required to meet FDA, OTC and Rx compliance in the U.S.

In order to demonstrate that the acne agent(s) in exemplary anhydrous hydrocolloid matrices that can be used as an acne treatment dressings alone and/or in combination with other elements (e.g., backing, liner, etc.), are homogeneously throughout the matrix itself, and as such, do not contain active "hot spots," a visual examination of the matrices can be made using a microscope.

Figure 4:
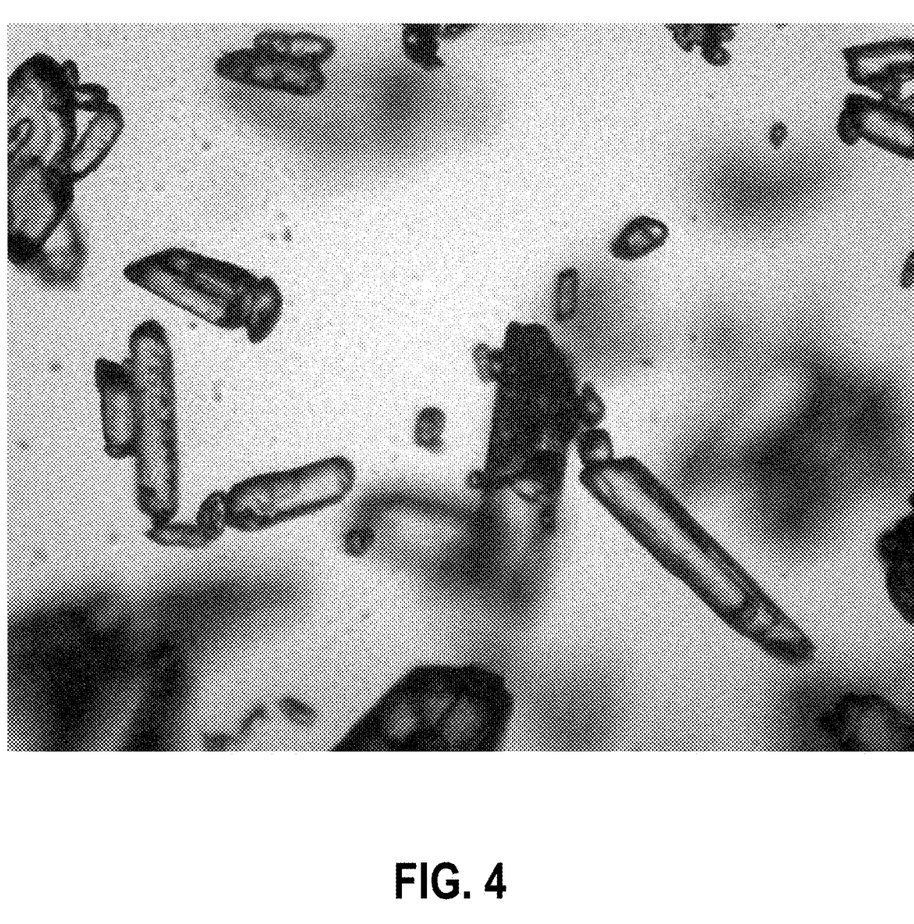
FIG. 4 shows a micrograph of salicylic acid crystals.

Referencing FIG. 4, a micrograph of salicylic acid crystals, prior to being added to a premix are shown at a 10× magnification. As can be seen in the micrograph, the salicylic acid crystals appear as elongated tubular structures.

Figure 5:
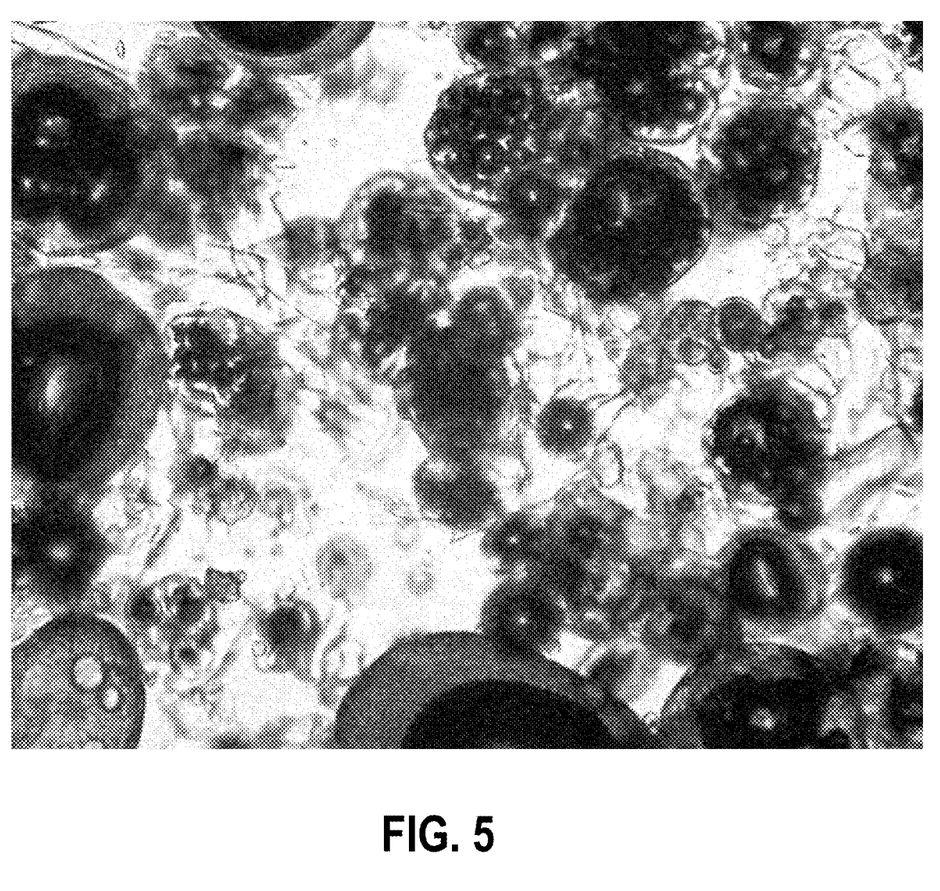
FIG. 5 shows a micrograph of a mixture of salicylic acid and skin care agents blended together as is known in the art.

FIG. 5 is a micrograph of a premix comprising salicylic acid and emollients that has been made by dry mixing the components of the premix together as is known in the art. As can be seen in the micrograph, the premix contains large, aggregated globules of emollients (black, spheres) and salicylic acid crystals unevenly distributed among the globules. It is believed that when the premix shown in FIG. 5 is added to and paddle mixed with bulk components of an anhydrous hydrocolloid matrix, the distribution of the emollients and salicylic acid crystals in the resulting anhydrous hydrocolloid matrix will remain uneven and even clump further together forming pockets of therapeutic agents, including "hot spots" of salicylic acid crystals. When such a resulting anhydrous hydrocolloid matrix is applied to the skin, inconsistent delivery of therapeutic actives to the skin occurs over time. As a result, it is believed that a release of a high load salicylic acid crystals from "hot spots" onto the skin within a short period of time (or all at once) results in yet further irritation of a consumer's skin, adding to a consumer's perception of harm and/or aversion to pain. This can be especially true when the actives that are delivered are for acne.

Figure 6:
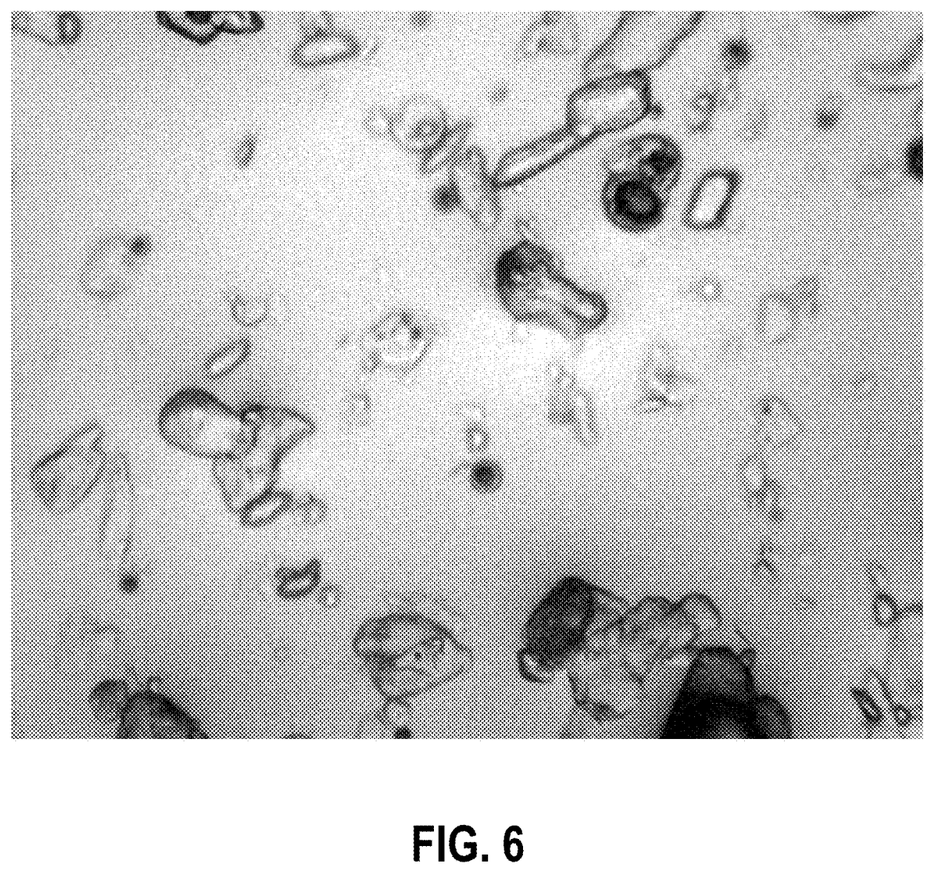
FIG. 6 shows a micrograph of an exemplary premix containing salicylic acid and skin care agents.

FIG. 6 is a micrograph of a premix having the identical chemical components as the premix shown in FIG. 5. However, the premix in FIG. 6 is made using an exemplary method as described herein. As can be seen in the micrograph, the premix does not contain large, aggregated globules of emollients (black, spheres) and salicylic acid crystals unevenly distributed among the globules. But rather, the micrograph shows small globules of emollients with salicylic acid crystals homogenously distributed throughout. It is believed that when the premix shown in FIG. 6 is added to and paddle mixed with bulk components of an anhydrous hydrocolloid matrix, the distribution of the emollients and salicylic acid crystals in the resulting anhydrous hydrocolloid matrix will remain even and will not clump together forming pockets of therapeutic agents, including "hot spots" of salicylic acid crystals. When such a resulting anhydrous hydrocolloid matrix is applied to the skin, consistent delivery of therapeutic actives to the skin occurs over time. As a result, it is believed that the even and relatively slow release of salicylic acid crystals occurs, minimizing further irritation of a consumer's skin, concurrently delivering skin care benefits to the consumer's skin over time.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those of ordinary skill in the art. For instance, the examples, embodiments, geometries, materials, dimensions, ratios, steps, and the like discussed above, are illustrative and are not required. Accordingly, the scope of the present invention should be considered in terms of any claims that may be presented and is understood not to be limited to the details of structure and operation shown and described in the specification and drawings.

We claim:
1. An acne treatment dressing comprising a laminate of:
 (a) a water impermeable or semi-water impermeable backing;
 (b) a release liner; and
 (c) an anhydrous hydrocolloid matrix comprising: (1) one or more therapeutic agents, (2) a premix and (3) bulk components of the anhydrous hydrocolloid matrix,
wherein:
  i. the one or more therapeutic agents includes an acne agent, wherein the acne agent consists of salicylic acid,
  that is present in the anhydrous hydrocolloid matrix at from about 0.5% to about 2% by weight of the anhydrous hydrocolloid matrix, and
  ii. the premix comprises a mixture of:
   A. a viscosity modifier selected from: cellulose, gums, chitosan, alginates, agars, gelatin, pectin, resins, polyisobutylene, styrene-olefin-styrene copolymers, styrene-isoprene-styrene copolymers and combinations thereof, and
   B. a hydrocarbon emollient selected from: liquid paraffin, dodecane, isododecane, isohexadecane, isoeicosane, petrolatum, microcrystalline wax, polyethylene, squalene, squalane, aliphatic hydrocarbons with monocarboxylic acid groups, sunflower oil, safflower oil, palm oil, jojoba oil, castor oil, terpenes, cyclohexasiloxane, cyclopentasiloxane and combinations thereof;
  iii. the anhydrous hydrocolloid matrix:
   A. comprises about 1 wt. % or less by weight of the hydrocolloid matrix of one or more cyclodextrins,
   B. is disposed between the backing and the release liner, and
   C. is configured to:
    1) absorb acne exudate, and
    2) release the one or more therapeutic agents;
  iv. each of the one or more therapeutic agents is encased within the anhydrous hydrocolloid matrix, as if, but not actually in a capsule, by the premix; and v. the premix encasing the therapeutic actives is homogenously distributed within the bulk components of the anhydrous hydrocolloid matrix.

2. An acne treatment dressing comprising a laminate of:
(a) a water impermeable or semi-water impermeable backing;
(b) a release liner; and
(c) an anhydrous hydrocolloid matrix, the anhydrous hydrocolloid matrix comprising: (1) one or more therapeutic agents, (2) a premix and (3) bulk components of the anhydrous hydrocolloid matrix, wherein:
  i. the one or more therapeutic agents are encased within the anhydrous hydrocolloid matrix as if, but not actually in, capsules formed:
    1) first by a premix comprising a mixture of:
      A. a viscosity modifier selected from: cellulose, gums, chitosan, alginates, agars, gelatin, pectin, resins, polyisobutylene, styrene-olefin-styrene copolymers, styrene-isoprene-styrene copolymers and combinations thereof, and
      B. a hydrocarbon emollient selected from: liquid paraffin, dodecane, isododecane, isohexadecane, isoeicosane, petrolatum, microcrystalline wax, polyethylene, squalene, squalane, aliphatic hydrocarbons with monocarboxylic acid groups, sunflower oil, safflower oil, palm oil, jojoba oil, castor oil, terpenes, cyclohexasiloxane, cyclopentasiloxane and combinations thereof; and
    2) second by bulk components of the anhydrous hydrocolloid matrix;
  ii. the premix encasing the one or more therapeutic agents is homogeneously distributed within the bulk components of the anhydrous hydrocolloid matrix;
  iii. the anhydrous hydrocolloid matrix is disposed between the backing and the release liner; and
  iv. the one or more therapeutic agents are selected from an acne agent, a skin conditioning agent and combinations thereof, wherein:
    1) the acne agent is selected from: salicylic acid, sulfur, resorcinal, resorcinol monoacetate and combinations thereof; and
    2) the skin conditioning agent is selected from: emollients, keratolytic agents, anti-inflammatory agents, anti-bacterial agents and combinations thereof.

3. The acne treatment dressing of claim 2, wherein the anhydrous hydrocolloid matrix comprises an acne agent, and the acne agent consists of salicylic acid.

4. The acne treatment dressing of claim 2, wherein the anhydrous hydrocolloid matrix comprises about 1 wt. % or less by weight of the hydrocolloid matrix of one or more cyclodextrins.

5. The acne treatment dressing of claim 1, wherein the anhydrous hydrocolloid matrix comprises by weight percentage of the anhydrous hydrocolloid matrix:
(a) from about 1% to about 5% of the viscosity modifier,
(b) from about 3% to about 8% of the hydrocarbon emollient, and
(c) from about 0.5% to about 16% of the one or more therapeutic agents.

6. The acne treatment dressing of claim 2, wherein the anhydrous hydrocolloid matrix comprises by weight percentage of the anhydrous hydrocolloid matrix:
(a) from about 1% to about 5% of the viscosity modifier,
(b) from about 3% to about 8% of the hydrocarbon emollient, and
(c) from about 0.5% to about 16% of the one or more therapeutic agents.

7. The acne treatment dressing of claim 3, wherein the salicylic acid is present in the hydrocolloid matrix at from about 0.5% to about 2% by weight of the anhydrous hydrocolloid matrix.

8. The acne treatment dressing of claim 7, wherein the anhydrous hydrocolloid matrix comprises about 1 wt. % or less by weight of the hydrocolloid matrix of one or more cyclodextrins.

9. The acne treatment dressing of claim 2, wherein the matrix is configured to:
(a) absorb acne exudate; and
(b) release the one or more therapeutic agents.

* * * * *